(12) United States Patent
Lindner et al.

(10) Patent No.: US 12,110,253 B2
(45) Date of Patent: Oct. 8, 2024

(54) SYSTEM AND METHOD OF CURING ADHESIVE DURING ASSEMBLY OF GLASS SYRINGES

(71) Applicant: ATS AUTOMATION TOOLING SYSTEMS INC., Cambridge (CA)

(72) Inventors: Roland Lindner, Winnenden (DE); Adrian Thorben Rupp, Winnenden (DE); Sukhanes Laopeamthong, Winnenden (DE)

( * ) Notice: Subject to any disclaimer, the term of this patent is extended or adjusted under 35 U.S.C. 154(b) by 518 days.

(21) Appl. No.: 17/346,714

(22) Filed: Jun. 14, 2021

(65) Prior Publication Data

US 2021/0300821 A1    Sep. 30, 2021

Related U.S. Application Data

(63) Continuation of application No. PCT/CA2019/051821, filed on Dec. 16, 2019.
(Continued)

(51) Int. Cl.
*C03C 27/04* (2006.01)
*A61M 5/31* (2006.01)
(Continued)

(52) U.S. Cl.
CPC .......... *C03C 27/048* (2013.01); *A61M 5/3129* (2013.01); *A61M 5/329* (2013.01);
(Continued)

(58) Field of Classification Search
CPC ... C03C 27/048; A61M 2207/10; A61M 5/34; A61M 5/349
(Continued)

(56) References Cited

U.S. PATENT DOCUMENTS

3,278,357 A   10/1966   Gettig et al.
3,788,321 A   1/1974    Reither et al.
(Continued)

FOREIGN PATENT DOCUMENTS

CA   3003689 A1    5/2017
DE   10252838 A1   6/2004
(Continued)

OTHER PUBLICATIONS

Extended European Search Report, European Patent Office, corresponding Europe Application No. 19897190.5, dated Jul. 13, 2022.
(Continued)

*Primary Examiner* — S. Behrooz Ghorishi
*Assistant Examiner* — Gregory C. Grosso
(74) *Attorney, Agent, or Firm* — Neil W. Henderson; Amarok IP Inc.

(57) ABSTRACT

A method for curing adhesive during assembly of glass syringes, including: dispensing adhesive onto a glass syringe; and curing the adhesive using a UV LED line array. The method may include one or both of pre-curing the adhesive using a UV LED spot and heating at least one of the glass barrel, needle and adhesive at one or more points during the method. A system for curing an adhesive during assembly of a glass syringe, the system including: a dispensing station for dispensing the adhesive onto a glass barrel and needle; a pre-curing station for pre-curing the
(Continued)

adhesive; a curing station for curing the adhesive; and at least one infrared heater for heating at least one of the glass barrel, needle and adhesive at one or more points in the system. The glass syringe may be operated on by a subset of the stations in the system.

17 Claims, 10 Drawing Sheets

Related U.S. Application Data (60) Provisional application No. 62/779,836, filed on Dec. 14, 2018.

(51) Int. Cl.
  *A61M 5/32* (2006.01)
  *C09J 4/00* (2006.01)
  *C09J 5/06* (2006.01)

(52) U.S. Cl.
  CPC . *C09J 4/00* (2013.01); *C09J 5/06* (2013.01); *A61M 2205/0238* (2013.01); *A61M 2205/368* (2013.01); *A61M 2207/00* (2013.01); *A61M 2207/10* (2013.01)

(58) Field of Classification Search
  USPC ...................................... 156/275.7
  See application file for complete search history.

(56) References Cited

U.S. PATENT DOCUMENTS

| | | | |
|---|---|---|---|
| 8,720,165 | B2 | 5/2014 | Skufca |
| 2002/0138042 | A1* | 9/2002 | Llorach ................. A61M 5/343 |
| | | | 422/26 |
| 2020/0009329 | A1* | 1/2020 | Daniel ................. B05D 3/0493 |
| 2020/0155867 | A1* | 5/2020 | Basiony ................ A61M 5/329 |

FOREIGN PATENT DOCUMENTS

| | | | |
|---|---|---|---|
| EP | 3894498 A4 | 8/2022 | |
| WO | WO-2004078477 A1 * | 9/2004 | ............ B41J 11/002 |

OTHER PUBLICATIONS

International Search Report, Canadian Intellectual Property Office as International Searching Authority, corresponding PCT Application No. PCT/CA2019/051821, dated Mar. 4, 2020.

Lindner, R.S. et al; "LED-generated UV for Adhesive curing in Medical Devices"; OndrugDelivery Magazine, dated Oct. 2, 2019, pp. 40-43, XP055718093.

Written Opinion, Canadian Intellectual Property Office as International Searching Authority, corresponding PCT Application No. PCT/CA2019/051821, dated Mar. 4, 2020.

* cited by examiner

SYSTEM AND METHOD OF CURING ADHESIVE DURING ASSEMBLY OF GLASS SYRINGES

RELATED APPLICATIONS

The present application is a continuation of PCT Application No. PCT/CA2019/051821, filed Dec. 16, 2019, which claims priority to U.S. Provisional Application No. 62/779,836 filed on Dec. 14, 2018, which are hereby incorporated herein by reference.

FIELD

The present disclosure relates generally to a system and method for curing adhesive. More particularly, the present disclosure relates to a system and method for curing adhesive when assembling a glass syringe.

BACKGROUND

Modern manufacturing and automation systems and processes are becoming more complex because these systems and processes are required to be fast, accurate and repeatable in order to provide appropriate product quality in short time frames. These systems and processes also seek to provide high machine efficiency with low downtime for maintenance, trouble-shooting, low cost per part and the like. For existing manufacturing and automation systems and processes, there is also a trend to provide on-going improvement in one or more of these factors in order to keep pace with the changing manufacturing environment.

One specific type of automation is glass syringe assembly in which a cannula is assembled with a glass barrel or hub using an adhesive. In the case of pharmaceuticals, it is important that surfaces of the glass syringe are not contaminated, which might otherwise contaminate any drug later stored in the syringe. Accordingly, there are regulatory organizations and standards organizations that specify the nature of the adhesive to be used with a pre-filled glass syringe. As an example, Loctite™ 3345 has received market approval as a packaging material for various drugs as it has been shown to be harmless for the patient as a part of the tested packaging for the drugs as well as being compatible with other packaging components over the shelf life of the syringe. As such, this adhesive is widely used in the glass syringe assembly. The adhesive is cured to provide a good bond between the metallic cannula and the glass barrel or hub. Typically, the adhesive is cured using a mercury lamp, which tends to be inefficient and costly. Further, mercury lamps can be harmful for the environment and are in the process of being phased out.

As such, there is a need for improved systems and methods for curing adhesive, particularly in operations such as assembly of glass syringes.

SUMMARY

According to one aspect herein, there is provided a method for curing adhesive during assembly of glass syringes, including: dispensing adhesive onto a glass syringe; pre-curing the adhesive using a UV LED spot; curing the adhesive using a UV LED line array; and heating the syringe.

According to an aspect herein, there is provided a method for curing adhesive during assembly of a glass syringe, the method including: dispensing the adhesive onto a glass barrel and needle; pre-curing the adhesive; curing the adhesive; and heating at least one of the glass barrel, needle and adhesive.

In some cases the method may further include: providing a vacuum to the glass barrel during the dispensing of the adhesive. The vacuum may assist in drawing the adhesive a predetermined distance into the space between the needle and the glass barrel.

In some cases the pre-curing may include shining a UV LED spot on the adhesive. In this case, the UV LED spot may be shined along the interior of the glass barrel. In this case, the glass barrel may refract the light such that the adhesive is irradiated from various angles.

In some cases the method may further include: introducing an inert gas around the glass barrel and needle during the curing of the adhesive. The inert gas is intended to replace oxygen in the vicinity of the adhesive. The inert gas may be directed at the adhesive area directly if the adhesive has been pre-cured.

In some cases the heating may be provided by an infrared lamp, infrared heater, or the like.

In some cases the heating is applied prior to dispensing the adhesive and during and after curing.

In some cases the method may further include: introducing an inert gas around the glass barrel and needle prior to dispensing the adhesive.

In some cases the curing may include irradiating the adhesive with an LED line array. The LED line array may include a plurality of LED lights having differing peak frequencies and spectrums.

According to another aspect herein, there is provided a method for curing adhesive during assembly of a glass syringe, the method including: dispensing the adhesive onto a glass barrel and needle; and curing the adhesive with an LED array while heating at least one of the glass barrel, needle and adhesive with infrared.

In some cases the method may further include: providing a vacuum to the glass barrel during the dispensing of the adhesive.

In some cases the method may further include: introducing an inert gas around the glass barrel and needle during the curing of the adhesive.

In some cases the method may further include: pre-curing the adhesive by shining a UV LED up the glass barrel.

In some cases the heating may be applied prior to dispensing the adhesive and during and after curing.

In some cases the method may further include: introducing an inert gas around the glass barrel and needle prior to dispensing of the adhesive.

According to another aspect herein, there is provided a system for curing an adhesive during assembly of a glass syringe, the system including: a dispensing station for dispensing the adhesive onto a glass barrel and needle; a pre-curing station for pre-curing the adhesive; a curing station for curing the adhesive; and at least one infrared heater for heating at least one of the glass barrel, needle and adhesive.

In some cases the dispensing station may include a vacuum pump to create a vacuum in the glass barrel during the dispensing of the adhesive.

In some cases the pre-curing station may include a UV LED spot directed longitudinally along the glass barrel toward the needle and the adhesive. In these cases, the UV LED spot may be positioned a predetermined distance from an opening of the glass barrel. In addition or alternatively, the UV LED spot may be positioned a predetermined distance from the adhesive.

In some cases the curing station may include at least one LED line array directed at the adhesive.

In some cases the at least one LED line array may include a plurality of LED lights having differing peak frequencies and spectrums.

In some cases the at least one LED line array is positioned a predetermined distance from the adhesive.

In some cases the curing station may include a housing for receiving the glass barrel and needle and one or more inert gas nozzles for directing an inert gas at the adhesive.

In some cases the at least one infrared heater applies heat toward the glass barrel and needle prior to dispensing the adhesive and during and after curing.

BRIEF DESCRIPTION OF FIGURES

Other aspects and features of the embodiments of the system and method will become apparent to those ordinarily skilled in the art upon review of the following description of specific embodiments in conjunction with the accompanying figures.

Embodiments of the system and method will now be described, by way of example only, with reference to the attached Figures, wherein.

DETAILED DESCRIPTION

The following description, with reference to the accompanying drawings, is provided to assist in understanding the example embodiments. The following description includes various specific details to assist in that understanding but these are to be regarded as merely examples. Accordingly, those of ordinary skill in the art will recognize that the various embodiments and changes and modifications thereto described herein can be modified without departing from the scope and spirit of the appended claims and their equivalents. In addition, descriptions of well-known functions and constructions may be omitted for clarity and conciseness.

The terms and words used in the following description and claims are not limited to their bibliographical meanings, but are meant to be interpreted in context and used to enable a clear and consistent understanding.

Generally, the present document provides for embodiments of a system and method for curing adhesive, for example during assembly of glass syringes. It will be understood that, while the examples herein relate to glass syringes, a similar system or method could be used for other situations where adhesive is applied in a smaller confined space and, in particular, to other medical devices/implements. In some cases, the method includes dispensing the adhesive, pre-curing the adhesive, and then curing the adhesive with at least one light emitting diode (LED) Ultraviolet (UV) light source. The method may also include heating the glass syringe, for example the glass barrel of the syringe, with an infrared heater or hot air.

Traditionally, glass syringes have been used in many pharmaceutical and drug related applications. In the development of an adhesive that would not affect the drug within the glass syringe, an appropriate adhesive was required. One example that is essentially an industry standard is the Loctite™ 3345 adhesive. Very few other adhesives have received the appropriate approvals and are considered appropriate to use with glass syringes. In particular, this may be, at least, in part due to the syringe being in contact with the drug as the syringe serves as packaging for the drug. Embodiments and examples herein make use of the Loctite 3345 adhesive as the example adhesive, but adhesives of similar compounds that may be approved for use in glass syringes may also benefit from the curing method and system detailed herein.

Conventional processes using this type of adhesive generally rely on mercury vapor lamps for curing. Unfortunately, mercury vapor lamps can have issues with high heat losses, extensive maintenance, product quality, repeatability issues and the like. In particular, it is known that mercury lamps have a short life expectancy and there is difficulty determining when they are beginning to perform at a degraded level. Thus, frequent maintenance is required, including replacing bulbs and reflectors. Further, mercury lamps provide output through a range of UV and Infrared wavelengths, produce significant heat output and often require suction, which consumes clean room air. As such, there is an incentive to move away from mercury lamps.

It has been determined that, adhesive curing, and in particular Loctite 3345 adhesive used on glass syringes, can require a particular combination of UV radiation and heat. Examples of suitable combinations may include UVC radiation, UVB radiation, UVA radiation, Infrared radiation, heat and time to result in a complete cure. Conventional mercury vapor lamps are able to incorporate various of these parameters but are now considered to be a less reliable method of producing UV radiation as noted above. Furthermore, assembly processes based on mercury lamps are also prone to defects, such as, surface bubbles, shrinkage, stress cracking, and the like (see, for example, FIGS. 8A and 8B). Some of these issues may arise due to overheating during curing.

Due to these and other issues, investigations and experimentation revealed that LED curing technologies may be effective. However, LEDs were not typically considered for adhesive curing because commercial LEDs are often limited to particular wavelengths in the UVA range and thus not typically suitable for curing adhesives like Loctite 3345, which requires a wider spectral range, such as what has provided by the mercury lamp, mainly from UVC to Infrared. Attempts to cure Loctite 3345 with LEDs often resulted in poor surface curing and quality issues due to the amount of leachable and/or extractable substances. Further, it was unclear which spectrums and which other factors from the mercury lamps were key to the curing process, and which were less required.

In reviewing LED technology, it was determined that this technology enabled a better means for process control and monitoring in contrast to conventional mercury lamps, and as a cold technology, can be more energy-efficient. Unfortunately, as commercial LEDs were unable to produce the complete wavelength spectrum of the mercury lamps, it was determined that further factors may need to be included with the LEDs. Factors such as Infrared wavelengths and heat were introduced to the system and it was determined that these factors were useful components for curing the adhesive, but that not all of the UV spectrum wavelengths were as required as previously thought. Further, with modern LED technology, it is possible to adjust the radiation intensity and time during the process, via a controller, allowing the radiation profile to be configured fitting to process requirements (for example, ramp or step functions). Moreover, the status of LED UV sources can be efficiently monitored (for example, on, off, output from 0% to 100%, false, internal temperature).

It will be understood that a UV LED may provide other benefits over traditional UV mercury lamps. For example, the UV lifetime is typically significantly higher and there is little to no waiting/warm up time when commencing use of the UV LEDs. Further, there is less maintenance required for UV LED systems when compared with traditional mercury lamps. There may be up to a 30 to 50% reduction in energy consumption to run a UV-LED when compared to running a Mercury vapor lamp and cooling system.

Figure 1:
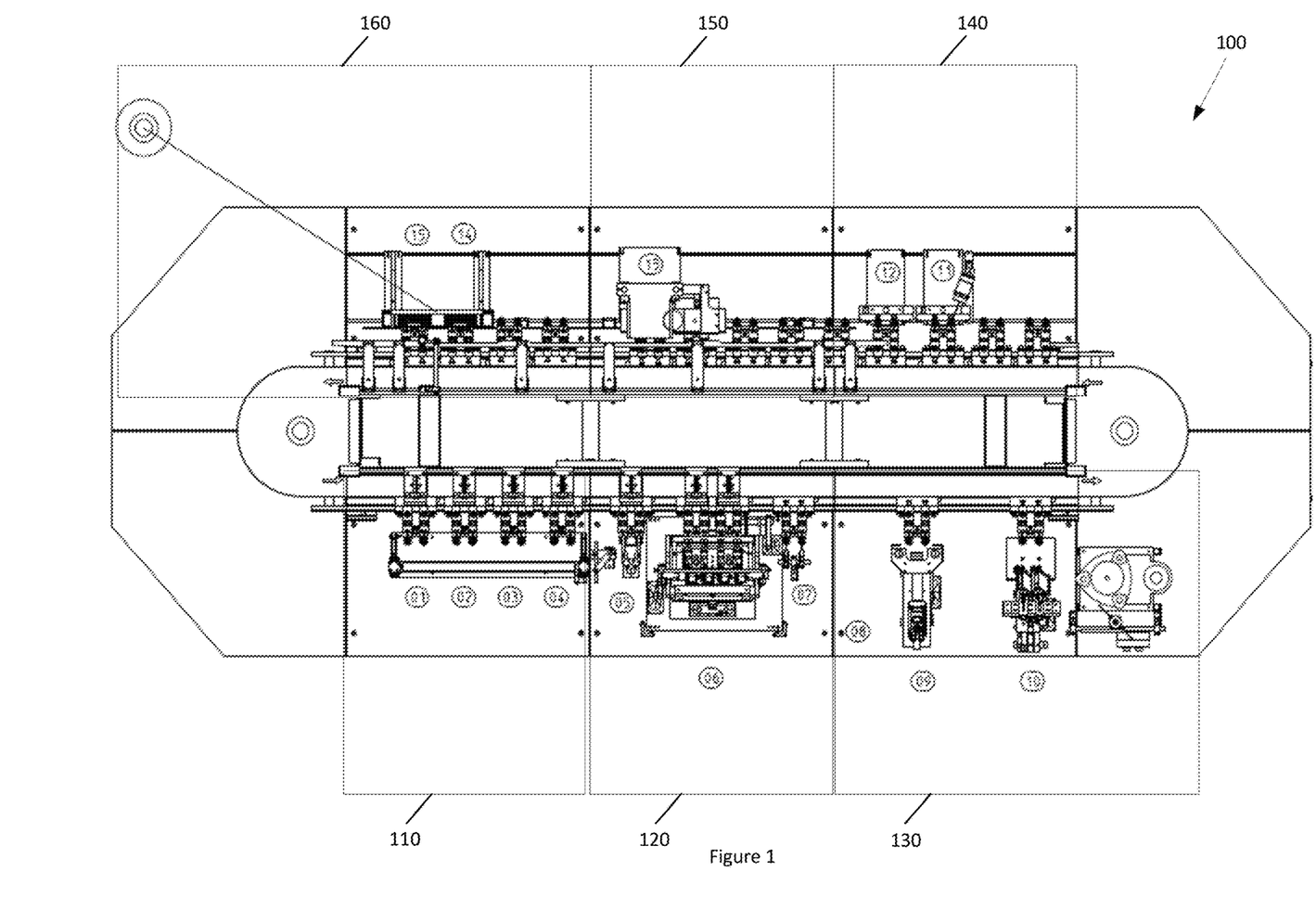
FIG. 1 illustrates a system for adhesive curing according to an embodiment.

FIG. 1 illustrates a system 100 for curing adhesive on glass syringes according to an embodiment. Generally speaking, the system includes an adhesive dispenser, and an UV-LED lamp. The system may include a heater intended to heat the glass syringe, for example, a glass barrel of a syringe. In some cases, the heater may be an infrared (IR) heater. The system may also include an LED light source, for example a line array or spot light, and/or mercury-vapor lamps.

In this particular embodiment, the system includes various stations or operations as follows: a loading station 110, where the glass barrel or the glass syringe is loaded; an insertion station 120, where a needle/cannula is inserted into the glass barrel and held in place with a gripper or the like; a dispensing station 130, where an adhesive is dispensed to attached the needle to the glass barrel; a pre-curing station 140, where the adhesive is pre-cured; a first curing station 150, where the adhesive is cured, optionally with infrared heating; and a second curing station 160, where the adhesive is cured, optionally while exposed to a flow of inert gas to reduce the amount of oxygen around the adhesive. In some cases only one of the first curing station and the second curing station may be used. In some cases, the pre-curing station may only be used with a selected one of the first curing station and the second curing station. In this type of system, the product (syringe) may be operated on at various stations depending on the process desired.

In some embodiments, the glass syringe may be heated by the heater prior to having the adhesive applied by the adhesive dispenser. Heat may be applied during later stages of the curing process or, in some cases, heat may be applied continuously and simultaneously to curing process throughout numerous stages. In some cases, there may be multiple heaters.

It is intended that the dispensed adhesive is applied to a bonding area, for example, an area between a glass barrel of a syringe and a needle or cannula. The depth of adhesive intake at bonding area and the adhesive contour (surface area) on the top of glass barrel may differ from product to product After the adhesive is applied, the at least one UV-LED lamp is used to cure the adhesive. In some cases, UV-LED spots may be used to pre-cure the adhesive prior to fully curing the adhesive. Pre-curing with a UV-LED spot initiates a bond between glass barrel and needle, intended to be strong enough so that the needle is held in place without a gripper for the full curing process. The needle is only held by a gripper in desired position during initial pre-curing to partially set the needle in place. Afterwards, the gripper can be opened and moved away so that the UV radiation from LED lamps can reach the adhesive from all sides without obstruction from the gripper or the like. Curing of remaining uncured adhesive may be completed using a linear array of UV-LED spots or UV-LED line array systems.

In some cases, the curing processes may involve UV radiation from LED lamps and may include simultaneous heat input, for example, using infrared heaters or other sources such as hot air. In still other cases, the curing processes may include an inflow or application of an inert gas. This may facilitate oxygen inhibition, leading to higher curing degree and/or curing yield of the adhesive.

In some cases, an infrared lamp may apply heating to the adhesive. The system may also have an LED line array that applies further LED UV radiation to cure the adhesive. In some cases, the system 100 may apply UVC radiation, for example, using a mercury lamp. Although, during experimentation, it was determined that the effect of UVC on surface curing was less significant than anticipated. As such, it is possible to cure various adhesives, including Loctite 3345, without the use of UVC radiation.

In some cases, the system may also include the ability to accompany the process with inert gas purging. By avoiding the use of hot air, and by including inert gas, it is intended that the oxygen exposure during the process may be minimized. In some cases, inert gas may only be applied during certain processes, such as during the application of heat. In other cases, inert gas may be applied during the full curing process. In some cases, purging may include the quantity of flow rate of a few milliliters per minute. It is expected that this process may be used for up to 20 seconds and may be placed approximately 2 mm to 20 mm from the surface of adhesive to be cured. In some cases, inert gas, for example nitrogen, is to be introduced through at least one nozzle. In a particular case, the inert gas may be introduced via two nozzles per glass syringe.

In some cases, vacuum suction may also be applied during the dispensing of adhesive. Vacuum suction is intended to allow the adhesive in the bonding area to have the right depth for the product. In some cases, preheating may be bypassed when vacuum suction is used.

Figure 2:
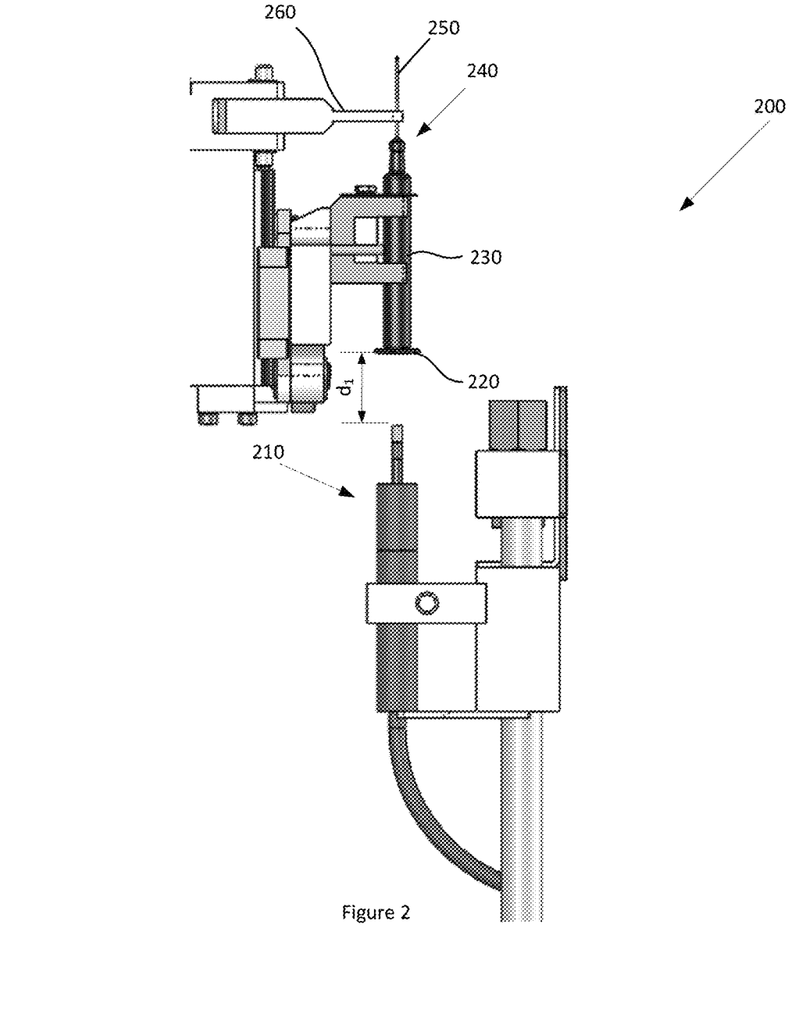
FIG. 2 illustrates a pre-curing station according to an embodiment.

FIG. 2 illustrates an embodiment of a pre-curing station 200, which includes a pre-curing LED spot 210 that is aimed at an opening 220 of the syringe barrel 230. The light from the LED spot 210 is directed at the adhesive area 240 to pre-cure the adhesive. In this embodiment, the LED spot 210 is directed inside the syringe barrel 230. The pre-curing allows the needle 250 to stay in place even after the gripper 260 is removed. In some cases, the LED spot 210 may be placed a predetermined distance $d_1$ from the opening 220. In some cases, the predetermined distance $d_1$ may be between approximately 0 mm and 80 mm from the bottom of the glass barrel. In other cases, it may be located between approximately 0 mm and 80 mm from the adhesive to be cured.

The glass body/barrel 230 is typically a uniform tube. In some cases, the LED spot or other pre-curing LED may not be directed directly to the adhesive area, but may be directed indirectly through the glass barrel 230. The glass barrel may direct the light to the adhesive area 240. In this case, due to a change in diameter of the rounded glass barrel 230, the light may be refracted at the adhesive area 240 and irradiate the adhesive. This may allow the adhesive to be exposed to 360 degree light.

Pre-curing can have various benefits. For example, pre-curing can allow the gripper(s) holding the needle/cannula to be released for easier access when curing the adhesive. Pre-curing can also accelerate the subsequent hardening processes. As the polymers are partially cross-linked they may react very quickly to further exposure. Further, the open side of the adhesive (transition glass barrel to cannula) is generally no longer completely liquid after pre-curing, but more likely to have a similar consistency as jelly, which provides more stability during curing. For example, without pre-curing, the inert gas may not be able to be blown in, because otherwise the gas flow may deform the adhesive. For pre-curing to occur, the distance of the LED spot from the glass barrel can be adjusted to obtain the appropriate intensity with a result of partially curing the adhesive. In some cases, the distance may be in the range of approximately 0-80 mm as noted above and the intensity may be approximately 25-100 mW/cm$^2$. In some cases the intensity may be approximately 35-80 mW/cm$^2$. In some cases, the intensity may be approximately 45-65 mW/cm$^2$.

Figure 3:
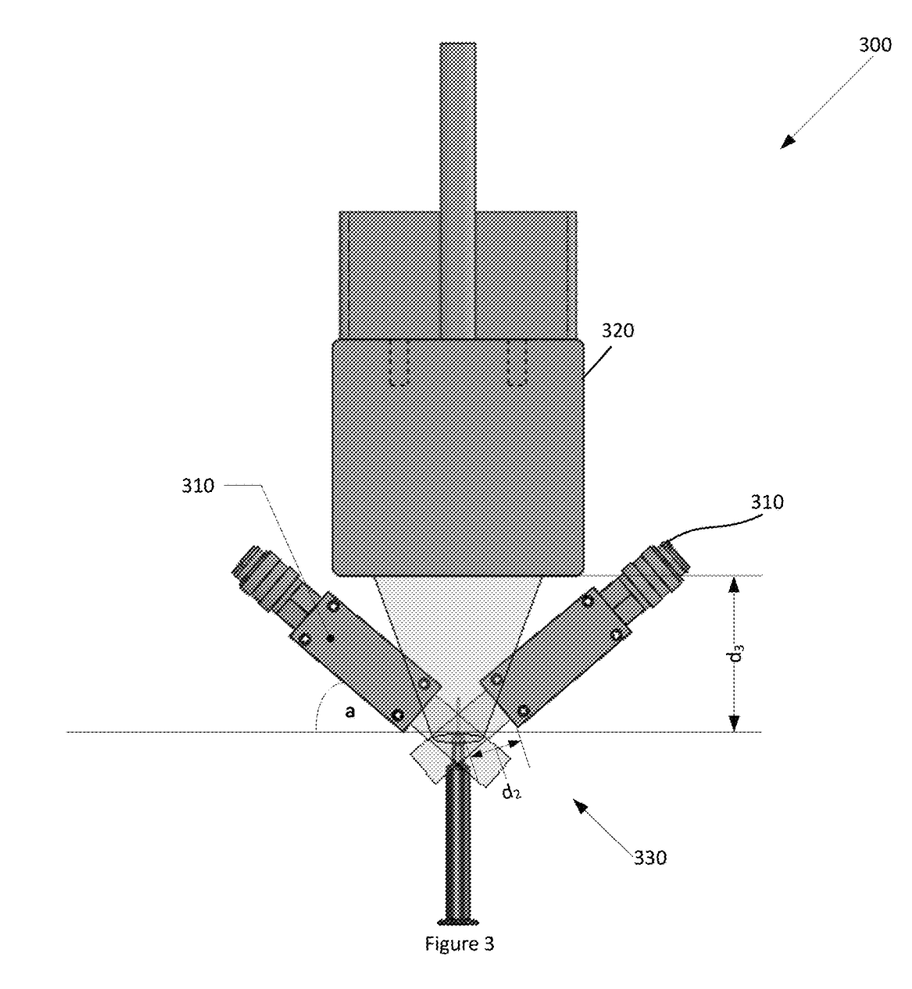
FIG. 3 illustrates a curing station with Infrared heat according to an embodiment.

FIG. 3 illustrates an embodiment of a curing station 300. In this embodiment, the curing station 300 includes at least one LED line array 310 in combination with at least one infrared heater/lamp 320. In this case, there are two LED line arrays 310, each placed at an angle, for example an angle of 10 degrees to 60 degrees from the horizontal to allow the infrared lamp to irradiate the adhesive area 330 at the same time as the LED line arrays 310. In some cases, the LED line array may be a predetermined distance $d_2$, for example, approximately 10 mm to 50 mm from the adhesive to be cured. The Infrared lamp can be placed another predetermined distance $d_3$, for example, between approximately 20 mm to 80 mm from the adhesive to be cured. In other cases, the infrared lamp may be approximately 20 to 80 mm from the needle tip.

In this case, the LED line array is associated with at least one Infrared heater/lamp. In some cases, the Infrared heater may produce a wavelength of between 700 and 1800 nm at an intensity of up to 2000 W. In some cases, the Infrared heating may last up to 20 seconds. In some cases, adding Infrared heat, curing with LED line array and purging with inert gas may be carried out simultaneously as described herein. In other cases, the infrared heating and, if using, the purging with inert gas may take place shortly before or after the LED line array is tuned on, for example with a time lapse of a few seconds. In some cases, purging with inert gas may not be required, and the adhesive may be cured without the inert gas.

Figure 4:
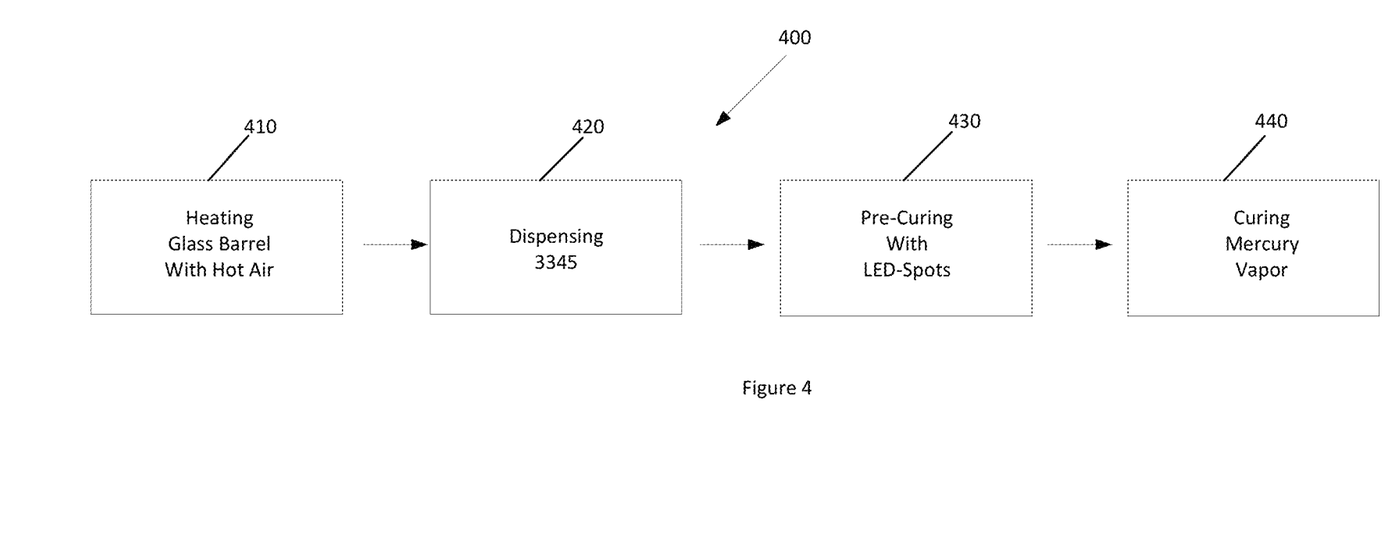
FIG. 4 illustrates a method for adhesive curing according to an embodiment.

FIG. 4 is a flowchart of an embodiment of a method for curing adhesive 400 according to an embodiment. The method 400 includes heating the product with hot air, for example heating the glass barrel of a syringe at 410. The adhesive is then dispensed on the product, for example Loctite 3345, at 420. An LED spot is then used to pre-cure the adhesive at 430. As noted above, pre-curing can allow the gripper holding the needle in place to be removed and is intended to reduce any shade that may be cast by the gripper on the adhesive area during curing. In some cases, pre-curing with at least one LED spot may provide for a UVA wavelength between 310 and 405 nm. In some cases, the wavelength is intended to be approximately 365 nm. The intensity may be up to 25 to 100 mW/cm$^2$ and may occur for about 6 seconds. In some cases, it may be for less than 6 seconds. After pre-curing, the adhesive may be further cured using, for example, mercury lamps, at 440, or using LED lights as described further below.

It is intended that the method for curing adhesive during assembly of glass syringes includes dispensing adhesive onto the glass syringes and pre-curing the adhesive using a UV LED spot curer, which includes at least one LED light spot. This may be conducted in combination with a vacuum suction and/or pre-heating of the glass barrel prior to dispensing the adhesive. Heat may be provided by an Infrared heater and/or hot air blower. The gripper(s) may then be removed from the glass syringes following pre-curing.

Curing the adhesive may include using a UV LED line array curing system consisting of at least one LED line array. In some cases, this may be applied in combination with at least one Infrared heater, either simultaneously or as a pre-treatment process to the curing. In some cases, inert gas insertion/purging, either continuously or a discrete inflow may be applied simultaneously or as a pre-treatment process. Inert gas insertion/purging may be performed either on the whole area or only partially at specific regions of the UV radiation field. Although the term purging may be used, it will be understood that only a predetermined amount of inert gas may be blown into the chamber or onto the adhesive surface and the system may not replace the whole volume of air by inert gas. In some cases, inert gas purging may not be applied during the curing process. Inert gas purging may be pressure and/or flow rate driven, allowing for desired flow patterns to be achieve via regulated valves and exchangeable or adjustable orifices. In some cases, post heating may also be applied using hot air and/or infrared heating.

Figure 5:
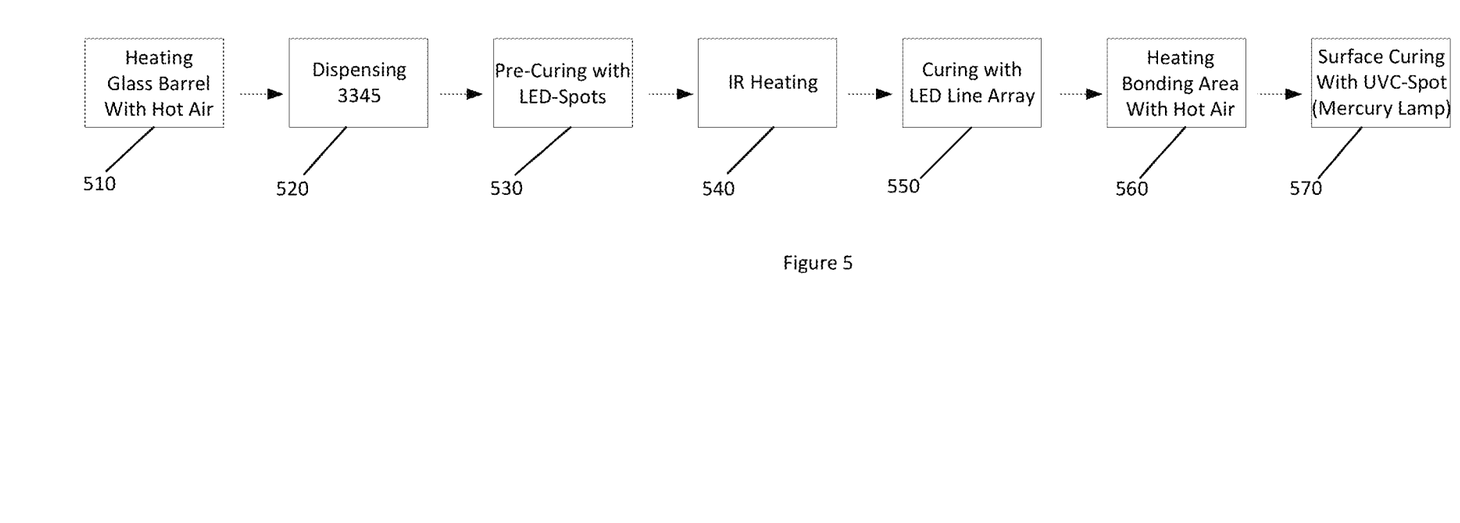
FIG. 5 illustrates another method for adhesive curing according to another embodiment.

FIG. 5 illustrates a method for curing adhesive 500 on glass syringes according to a further embodiment. At 510, the glass syringe may be heated, for example, with hot air. AT 520, adhesive is applied to the product. At 530, the product may then be exposed to pre-curing with one or more LED-Spots. In some cases, the wavelength may be approximately 365 nm. In some cases, at 540, the product may then be exposed to infrared heating. At 550, curing could then continue with an LED line array, in an effort to further reduce the reliance on a mercury lamp. In some cases, the LED line array curing may be in connection with the Infrared heating. In other cases, these processes may occur separately. In some cases, curing with an LED line array may provide for a UVA wavelength between 310 and 405 nm. In some cases, the wavelength may be provided by various LED lights having wavelengths of, for example, 365 nm, 385 nm, 395 nm or 405 nm. It is intended that the intensity of the LED line array may be up to 8000 mW/cm$^2$ and may occur for up to 20 seconds. In other cases, it may be cured for under 20 seconds. In some cases, at 560, the adhesive/bonding area could receive further hot air from an infrared lamp or from another heat source. At 570, the product may then have further surface curing, for example, to provide for UVC spot curing, for example, via a mercury lamp.

Figure 6:
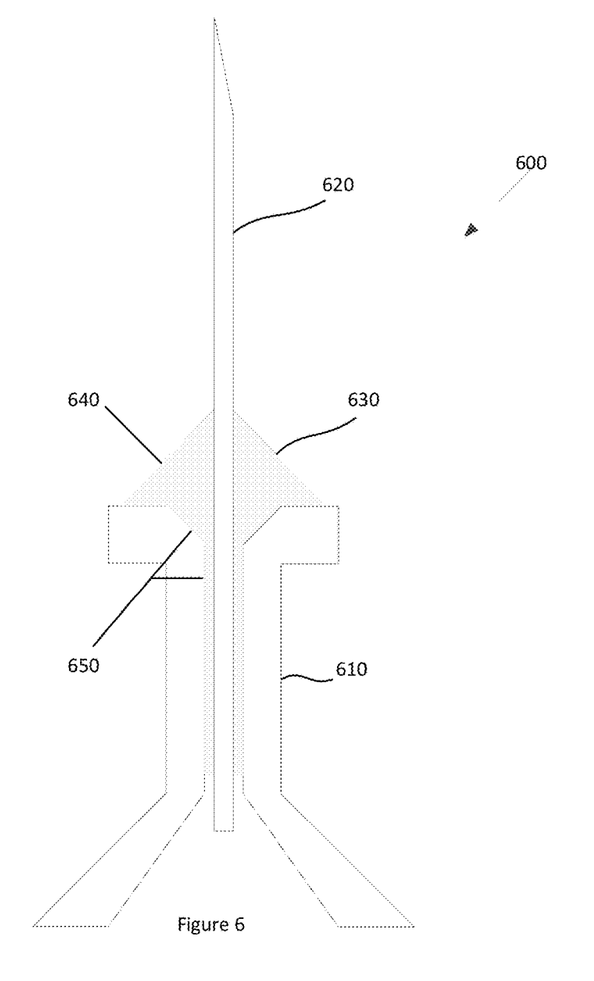
FIG. 6 illustrates an example of adhesive areas to be cured on a glass syringe.

FIG. 6 illustrates an example glass syringe 600, including a glass barrel 610 (only a portion is shown) and a needle 620. The needle 620 is attached to the glass barrel 610 with an adhesive 630. The adhesive 630 includes a bonding area 640, between the needle 620 and glass barrel 630, and a surface area 650, which is outside the glass barrel 610. The adhesive 630 is typically applied as a liquid and requires curing to complete the process. Curing is intended to properly position the needle and also avoid leaks to or from the medication, which, if present could result in contamination. In general, the curing should be performed in a manner to avoid damage to the needle or syringe barrel in order to maintain the integrity of the product. As the bonding area 640 and surface area 650 may each be exposed to oxygen to a different extent, different curing conditions may be required.

Figure 7:
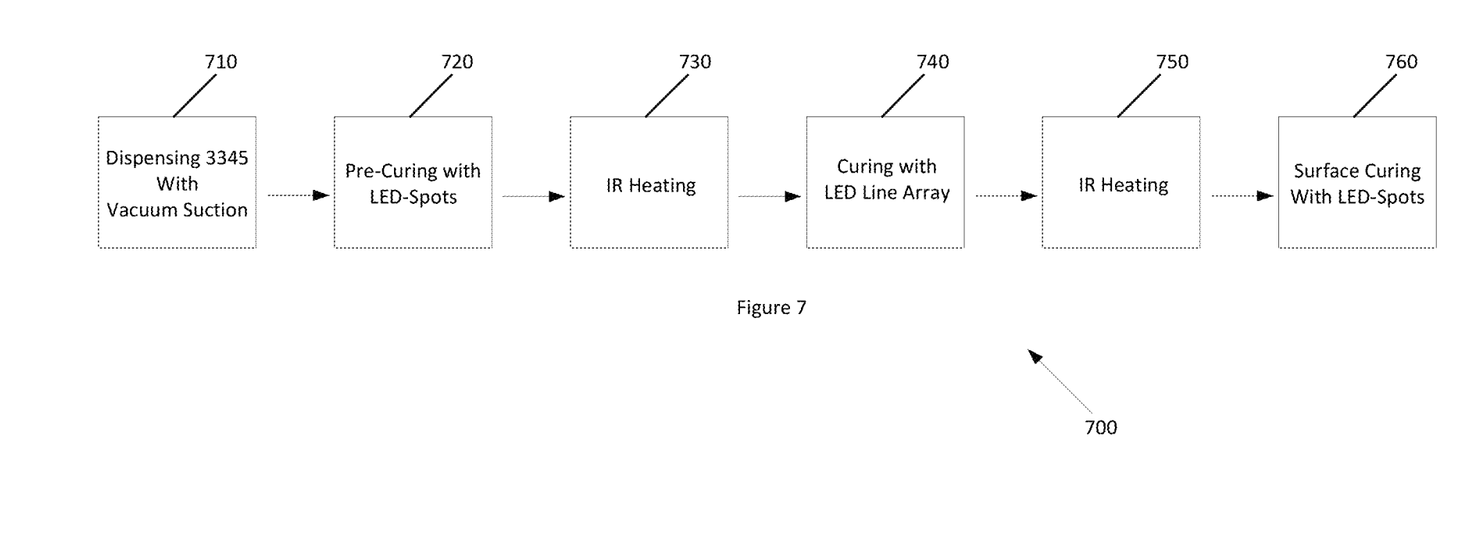
FIG. 7 illustrates yet another method for adhesive curing according to an embodiment.

FIG. 7 illustrates yet another method for curing adhesive 700 according to another embodiment. In this embodiment, at 710 the adhesive, for example Loctite 3345 adhesive, may be dispensed with vacuum suction to draw the adhesive into the glass barrel. For example, the vacuum suction may aid in ensuring that the adhesive in the bonding area has an appropriate depth. At 720, the bonding area may be pre-cured by at least one LED spot, which is positioned below the glass barrel in a manner that the focal point of radiated light is at or near the bonding area shown in FIG. 6. As noted herein, the product may receive infrared heating (730, 750), prior to, in addition to and/or after being cured. At 740, the curing may be completed without the use of a mercury lamp and may rely more on LED curing technology, which may, for example, provide UVA light with one or more peaks at, for example, 365 nm, 385 nm, 395 nm or 405 nm. At 760, the product may also have surface area curing applied by the LED line array. In this example, the bonding area is pre-cured but the whole adhesive area could also be pre-cured. It will be understood that the particular wavelengths for the LED lights used in the system and method will be selected based on the type of adhesive used. The numerical values provided are generally intended for the example of Loctite 3345 adhesive.

Figure 8A:
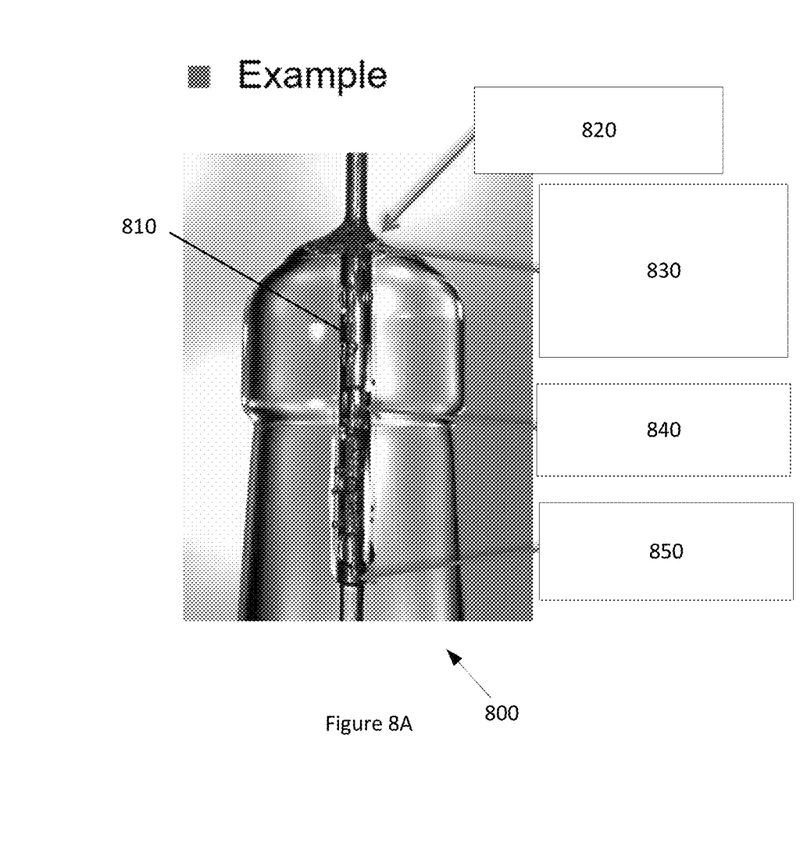
FIGS. 8A and 8B illustrate examples of issues that can occur with adhesive curing.
Figure 8B:
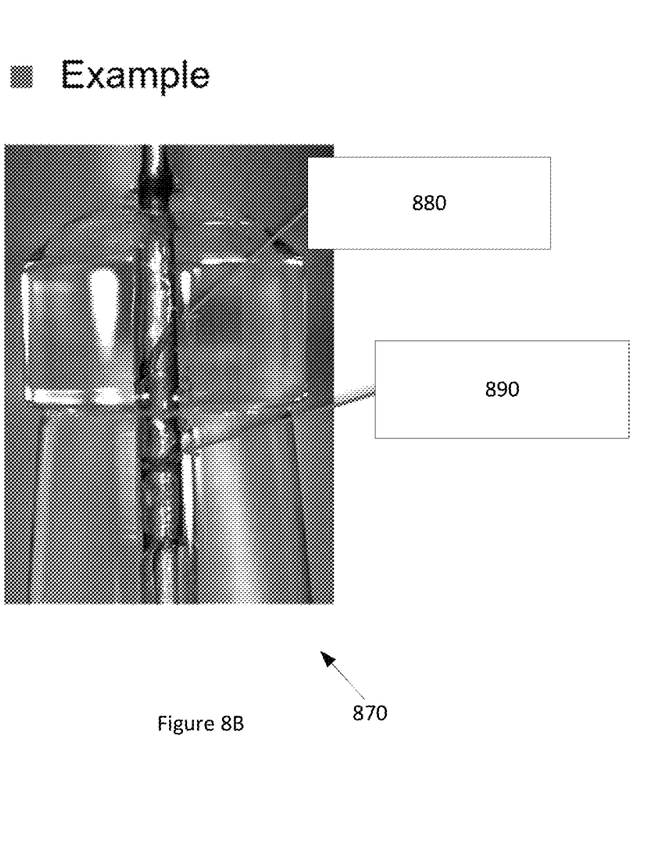

In a particular example, the embodiments of the method and system disclosed herein are intended to be used for curing adhesive to a glass syringe that may be used in the medical or pharmaceutical field. As noted herein, conventional methods generally rely on mercury lamps, which are typically inefficient, tend to produce waste heat, and have other issues. It has been noted that other methods have been attempted but have been determined to create issues and may not lead to a satisfactory quality assurance level. In particular, conventional methods have led to issues as shown in FIGS. 8A and 8B. FIG. 8A shows a portion of a syringe 800 in which the adhesive 810 can be seen to have an unequal dome 820, surface bubbles on the dome 830, which may have been caused by having the adhesive too warm, shrinkage bubbles near the needle 840, which may compromise the structure of the syringe, and a closed or partially closed cannula 850. Further, FIG. 8B shows a portion of another syringe 870 having other issues such as helical stress cracking 880 and horizontal stress cracking 890, which may compromise the integrity of the adhesive and the associated product. These physical attributes have a substantial influence on the mechanical properties of the product, e.g. pull-out force of the needle or cannula. A further relevant issue is the level of leachables and extractables (residual monomer content or remaining uncured adhesive) on the product. An analysis of the residual monomer content can be used to determine the extent of chemical hardening and can be adjusted to meet a customer requirement or the like.

Figure 9:
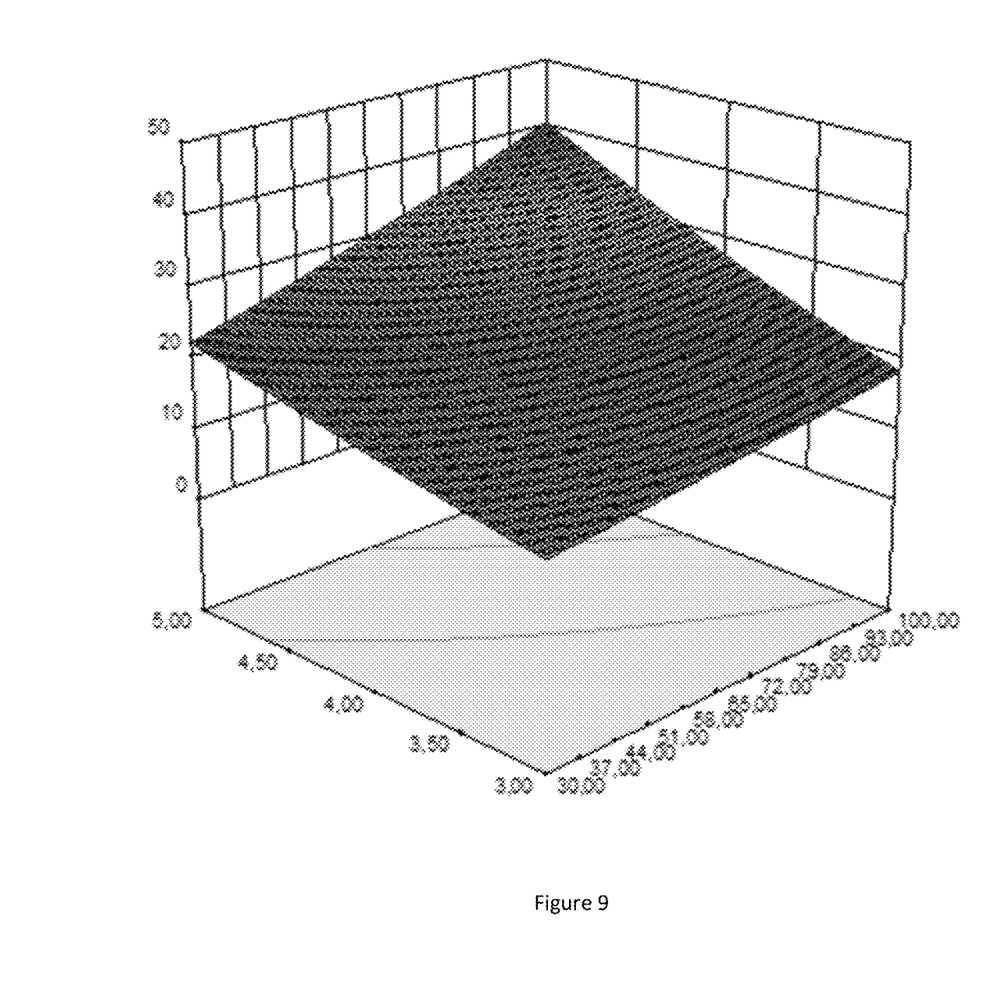
FIG. 9 shows a graph illustrating the relationship between temperature, time and intensity.

FIG. 9 illustrates a general relationship among temperature, time and intensity for curing. It will be understood that the curing is intended to completely seal the area between the needle and glass barrel with the adhesive. The cured adhesive is intended to not exhibit an amount of residual monomer above an allowable limit, when the product is complete. It will be understood that the product, for example a syringe, may be improved in various optical and mechanical properties, although the adhesive may limit the optical properties of the product. Adhesive curing is influenced by many factors, including, for example, UVC, UVB, UVA, IR, time, heat, product surface, gap width, intensity, geometry, oxygen exposure, and the like.

Figure 10:
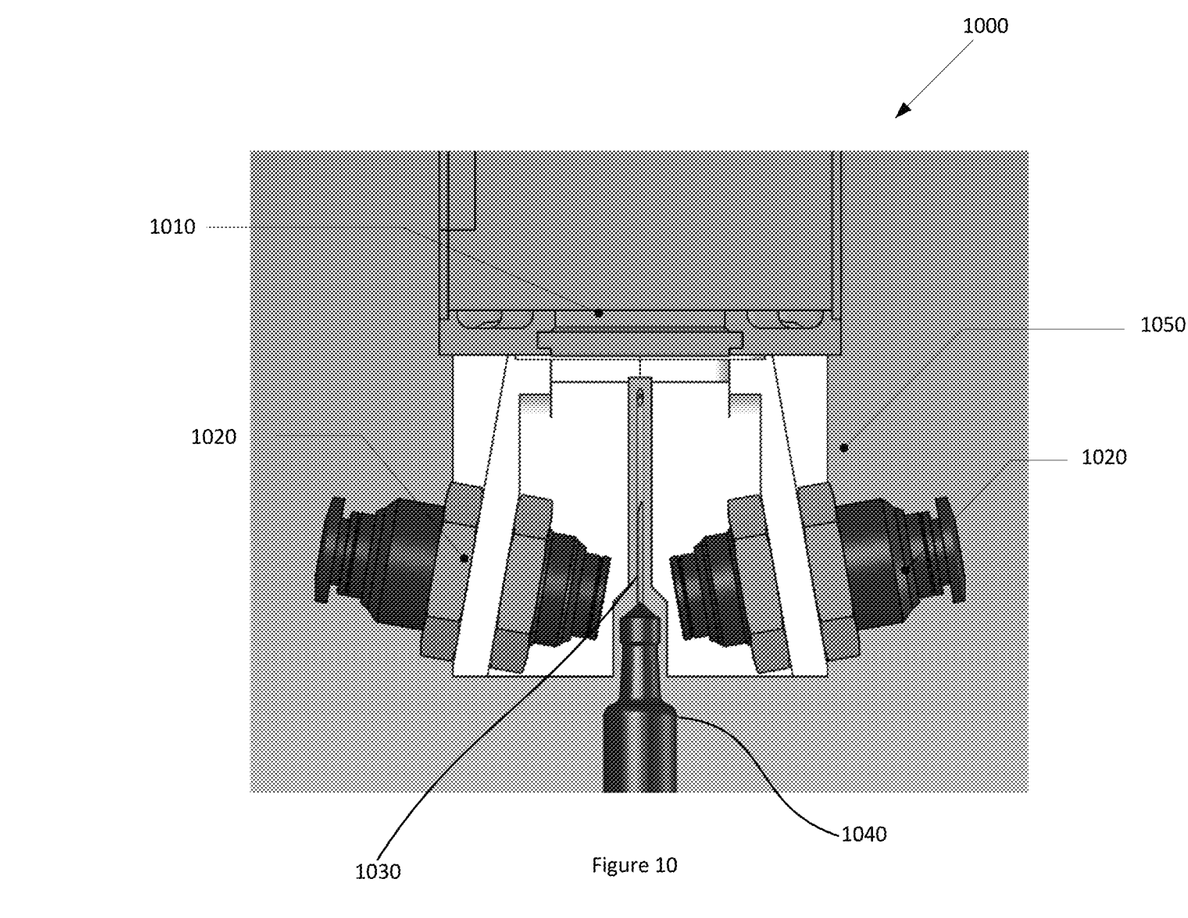
FIG. 10 illustrates a curing station including a UV LED Line array with an inert gas according to an embodiment.

FIG. 10 illustrates another curing station 1000, making use of inert gas, according to an embodiment herein. The curing station 1000 includes an LED line array 1010 (or may be infrared heating or a combination of both) and at least one inert gas nozzle 1020. The curing station 1000 operates on a needle 1030 and glass syringe 1040. In this embodiment, by introducing an inert gas, such as nitrogen or the like, into the area around the adhesive it is intended that any oxygen exposure during the curing process may be reduced/minimized. In some cases, the quantity of flow rate of the inert gas may be a few milliliters per minute.

The curing station 1000 may also include a housing 1050. In the case of using a housing 1050, the inert gas can substantially fill the area around the adhesive as it is cured. When using inert gas nozzles (rather than a sealed chamber filled with inert gas), it may be preferable to have the adhesive pre-cured so that the flow of inert gas does not deform the adhesive or move the needle in relation to the glass barrel. The use of a flow of inert gas can be preferable to having to enclose the glass syringe in an inert environment during curing as the process can proceed more quickly and efficiently. The inert gas flow may occur through one or more nozzles (2 shown in FIG. 10) at a rate in the range of, for example, 0.03 $Nm^3/h$ to 0.2 $Nm^3/h$. The nozzles may be placed approximately 2 mm to 20 mm from the surface of adhesive to be cured. The inert gas may be introduced for a predetermined time during curing, for example, in the range of approximately 20s. The use of inert gas may be effective during the application of heat and/or during the full curing process.

Figure 11:
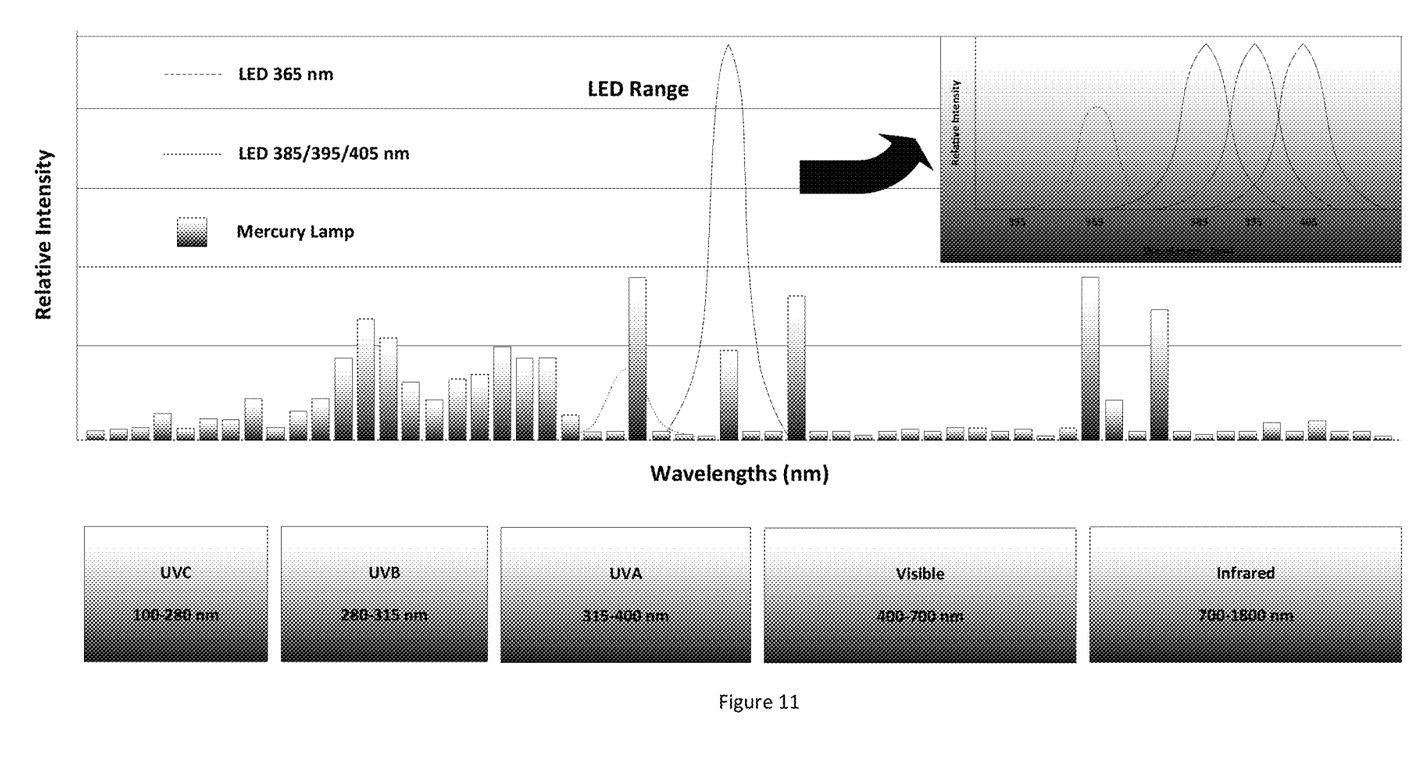
FIG. 11 illustrates relative wavelengths for different curing light options.

FIG. 11 illustrates the range of wavelengths of UV light that can be produced by a mercury lamp as well as by example LED lights. In some cases, the LED lights can be chosen to form an array including a plurality of peak wavelengths in order to have a broader spectrum of coverage. In some cases, the LED lights used for pre-curing will have a different wavelength(s) than those used for curing. In FIG. 11, as an example, an LED spot having a peak at 365 nm may be used for pre-curing and an LED array having peaks at 385/395/405 nm may be used for curing. In some cases, the LED array may also include an LED light with a peak at 365 nm to give a broader spectrum of coverage.

While various reference numerals have been used to identify various elements in the embodiments, it will be understood that a similar term used to refer to elements having different reference numerals will generally refer to the same type of element and that elements may be interchangeable among the embodiments as would be known to one of skill in the art.

In the preceding description, for purposes of explanation, numerous details are set forth in order to provide a thorough understanding of the embodiments of the invention. However, it will be apparent to one skilled in the art that these specific details are not required in order to practice the invention. In other instances, well-known electrical structures and circuits are shown in block diagram form in order not to obscure the invention.

The above-described embodiments of the invention are intended to be examples only. Alterations, modifications and variations can be effected to the particular embodiments by those of skill in the art without departing from the scope of the invention, which is defined solely by the claims appended hereto.

What is claimed is:

1. A method for curing adhesive during assembly of a glass syringe, the method comprising:
dispensing the adhesive onto a glass barrel and needle;
pre-curing the adhesive, wherein the pre-curing comprises directing a UV LED spot longitudinally along the glass barrel toward the needle and the adhesive;
curing the adhesive; and
heating at least one of the glass barrel, needle and adhesive.

2. A method according to claim 1 further comprising: providing a vacuum to the glass barrel during the dispensing of the adhesive.

3. A method according to claim 1 further comprising: introducing an inert gas around the glass barrel and needle during the curing of the adhesive.

4. A method according to claim 1 wherein the heating is provided by an infrared lamp.

5. A method according to claim 1 wherein the heating is applied prior to dispensing the adhesive and during and after curing.

6. A method according to claim 1 further comprising: introducing an inert gas around the glass barrel and needle prior to dispensing the adhesive.

7. A method according to claim 1 wherein the curing comprises irradiating the adhesive with an LED line array.

8. A method for curing adhesive during assembly of a glass syringe, the method comprising:
dispensing the adhesive onto a glass barrel and needle; and
curing the adhesive with an LED array while heating at least one of the glass barrel, needle and adhesive with infrared.

9. A system for curing an adhesive during assembly of a glass syringe, the system comprising:
a dispensing station for dispensing the adhesive onto a glass barrel and needle;
a pre-curing station for pre-curing the adhesive, wherein the pre-curing station comprises a UV LED spot directed longitudinally along the glass barrel toward the needle and the adhesive;
a curing station for curing the adhesive; and
at least one infrared heater for heating at least one of the glass barrel, needle and adhesive.

10. A system according to claim 9 wherein the dispensing station comprises a vacuum pump to create a vacuum in the glass barrel during the dispensing of the adhesive.

11. A system according to claim 9 wherein the UV LED spot is positioned a predetermined distance from an opening of the glass barrel.

12. A system according to claim 9 wherein the UV LED spot is positioned a predetermined distance from the adhesive.

13. A system according to claim 9 wherein the curing station comprises at least one LED line array directed at the adhesive.

14. A system according to claim 13 wherein the at least one LED line array comprises a plurality of LED lights having differing peak frequencies and spectrums.

15. A system according to claim 13 wherein the at least one LED line array is positioned a predetermined distance from the adhesive.

16. A system according to claim 9 wherein the curing station comprises a housing for receiving the glass barrel and needle and one or more inert gas nozzles for directing an inert gas at the adhesive.

17. A system according to claim 9 wherein the at least one infrared heater applies heat toward the glass barrel and needle prior to dispensing the adhesive and during and after curing.

* * * * *